United States Patent [19]

Grasselli et al.

[11] 4,192,776
[45] Mar. 11, 1980

[54] CATALYSTS AND PROCESS FOR THE AMMOXIDATION OF OLEFINS

[75] Inventors: Robert K. Grasselli, Chagrin Falls; Arthur F. Miller; Harley F. Hardman, both of Lyndhurst, all of Ohio

[73] Assignee: The Standard Oil Company, Cleveland, Ohio

[21] Appl. No.: 866,203

[22] Filed: Jan. 3, 1978

Related U.S. Application Data

[60] Division of Ser. No. 735,859, Oct. 27, 1976, which is a continuation-in-part of Ser. No. 426,175, Dec. 19, 1973, abandoned, which is a continuation-in-part of Ser. No. 85,722, Oct. 30, 1970, abandoned.

[51] Int. Cl.$^2$ .................. B01J 21/02; B01J 27/14; B01J 23/10; B01J 23/84

[52] U.S. Cl. .................. 252/432; 252/435; 252/437; 252/462; 252/468; 252/470; 252/473; 260/465.3

[58] Field of Search ............... 252/432, 435, 437, 462, 252/468, 470, 473

[56] References Cited

U.S. PATENT DOCUMENTS 3,639,269  2/1972  Koberstein et al. ............ 252/437

Primary Examiner—Delbert E. Gantz
Assistant Examiner—William G. Wright
Attorney, Agent, or Firm—John E. Miller, Jr.; Herbert D. Knudsen; Larry W. Evans

[57] ABSTRACT

Catalysts containing a rare earth, tantalum or niobium plus iron, bismuth and molybdenum and at least one element of nickel, cobalt, magnesium, zinc, cadmium or calcium are especially effective for the ammoxidation of olefins.

6 Claims, No Drawings

CATALYSTS AND PROCESS FOR THE AMMOXIDATION OF OLEFINS

CROSS REFERENCE TO RELATED APPLICATION

This application is a divisional application of application Ser. No. 735,859, filed Oct. 27, 1976, which is a continuation-in-part of our prior application Ser. No. 426,175, filed Dec. 19, 1973, now abandoned, which in turn is a continuation-in-part of our prior application Ser. No. 85,722, filed Oct. 30, 1970, now abandoned.

BACKGROUND OF THE INVENTION

The catalysts of this invention have a high activity for the production of unsaturated nitriles at a relatively low reaction temperature. This high activity at a low reaction temperature is surprising in view of U.S. Pat. No. 2,904,580 issued Sept. 15, 1959, which discloses a process for the production of acrylonitrile from propylene and ammonia in the presence of a catalyst selected from the group consisting of bismuth, tin and antimony salts of molybdic and phosphomolybdic acids and bismuth phosphotungstate, and U.S. Pat. No. 3,226,422 issued Dec. 28, 1965, which discloses a catalyst comprising the oxides of iron, bismuth, molybdenum and phosphorus for the production of unsaturated nitriles from olefin-ammonia mixtures.

In addition to high activity for nitrile production, the catalyst employed in the process of this invention has a number of other important advantages that contribute greatly to the efficient and economic operation of the process. The catalyst has excellent redox stability under the reaction conditions of the process. This permits the use of low process air to olefin ratios and high weight hourly space velocities. The catalyst exhibits efficient ammonia utilization thus greatly reducing the amount of unreacted ammonia appearing in the reactor effluent and thus lowering the amount of sulfuric acid required to neutralize the ammonia in the effluent. Improvements are obtained in the recovery section operation and pollution control resulting from the lowering of polymer waste products that are formed. The catalyst performs optimally at a lower reactor temperature than is normally employed for this type of reaction with per pass conversions to the nitrile product as high as 80 percent and above. Use of lower operating temperatures favors longer catalyst life and minimizes effluent problems such as afterburning. Ease of catalyst preparation and lower cost of the essential catalytic components are additional benefits that can be realized with the use of the catalyst of this invention.

SUMMARY OF THE INVENTION

The present invention is catalysts described by the formula

$A_aD_gE_bG_cFe_dBi_eMo_{12}O_x$

Wherein
  A is a rare earth metal, tantalum, niobium or mixture thereof;
  D is an alkali metal;
  E is nickel, cobalt, magnesium, zinc, cadmium, calcium or mixture thereof;
  G is phosphorus, boron, arsenic or mixture thereof; and wherein
  a is greater than zero to about 3;
  b is about 0.1 to about 20;
  c and g are 0 to about 3;
  d is about 0.1 to about 8;
  e is about 0.1 to about 6;
  f is about 8 to about 16; and
  x is a number determined by the valence requirements of the other elements present.

Another facet of this invention is the use of these catalysts in the known ammoxidation of propylene or isobutylene.

The catalyst is any catalyst described by the empirical formula above. Preferred catalysts are those that contain nickel, cobalt or magnesium, i.e. where B is nickel, cobalt or magnesium, with those catalysts containing nickel and cobalt being especially preferred. Also preferred are those catalysts wherein C represents phosphorus, arsenic or mixtures thereof.

The catalyst of this invention may be prepared by any of the numerous methods of catalyst preparation which are known to those skilled in the art. For example, the catalyst may be manufactured by co-gelling the various ingredients. The co-gelled mass may then be dried and ground to an appropriate size. Alternately, the co-gelled material may be slurried and spray dried in accordance with convention techniques. The catalyst may be extruded as pellets or formed into spheres in oil as is well known in the art. Alternatively, the catalyst components may be mixed with the support in the form of the slurry followed by drying, or may be impregnated on silica or other supports.

The alkali metal may be introduced into the catalyst as an oxide or as any salt which upon calcination will yield the oxide. Preferred salts are the nitrates which are readily available and easily soluble.

Bismuth may be introduced into the catalyst as an oxide or as any salt which upon calcination will yield the oxide. Most preferred are the water-soluble salts which are easily dispersible within the catalyst and which form stable oxides upon heat-treating. The most preferred salt for introducing bismuth is bismuth nitrate.

To introduce the iron component into the catalyst one may use any compound of iron which, upon calcination, will result in the oxides. As with the other elements, water-soluble salts are preferred for the ease with which they may be uniformly dispersed within the catalyst. Most preferred is ferric nitrate. Cobalt, nickel, magnesium, zinc, cadmium, calcium and the rare earth metals are similarly introduced.

To introduce the molybdenum component, any molybdenum oxide such as the dioxide, trioxide, pentoxide, or sesquioxide may be used; more preferred is a hydrolyzable or decomposable molybdenum salt such as a molybdenum halide. A preferred starting material is ammonium heptamolybdate.

Arsenic may be introduced as orthoarsenic acid. Other elements may be introduced, starting with the metal, oxidizing the metal with an oxidizing acid such as nitric acid, and then incorporating the nitrate into the catalyst. Generally, the nitrates are readily available and form a very convenient starting material.

Other variations in starting materials will suggest themselves to one skilled in the art, particularly when the preferred starting materials mentioned hereinabove are unsuited to the economics of large-scale manufacture. In general, any compounds containing the desired catalyst components may be used provided that they result, upon heating to a temperature within the range disclosed hereinafter, in the oxides of the instant catalyst.

The catalyst can be employed without a support and will display excellent activity. It also can be combined with a support, and preferably at least 10 percent up to about 90 percent of the supporting compound by weight of the entire composition is employed in this event. Any known support materials can be used, such as, for example, silica, alumina, zirconia, titania, alundum, silicon carbide, alumina-silica, and the inorganic phosphates, silicates, aluminates, borates and carbonates which are stable under the reaction conditions to be encountered in the use of the catalyst.

The catalytic activity of the system is enhanced by heating at an elevated temperature. Generally, the catalyst mixture is dried and heated at a temperature of from about 750° to about 1850° F., preferably at about 900° to 1300° F., for from one to twenty-four hours or more. If activity then is not sufficient, the catalyst can be further heated at a temperature above about 1000° F. but below a temperature deleterious to the catalyst at which it is melted or decomposed. Usually this limit is not reached before 2000° F., and in some cases this temperature can be exceeded.

In general, the higher the activation temperature, the less time required to effect activation. The sufficiency of activation at any given set of conditions is ascertained by a spot test of a sample of the material for catalytic activity. Activation is best carried out in an open chamber, permitting circulation of air or oxygen, so that any oxygen consumed can be replaced.

Further, pre-treatment or activation of the catalyst before use with a reducing agent such as ammonia in the presence of a limited amount of air at a temperature in the range of 550° to 900° F. is also beneficial.

A preferred method of preparing the catalyst of this invention will be described hereinafter in connection with the Specific Embodiments of the invention.

In the ammoxidation, the reactants employed in producing the unsaturated nitriles of this invention are oxygen, ammonia and an olefin having only three carbon atoms in a straight chain such as propylene or isobutylene or mixtures thereof.

The olefins may be in admixture with paraffinic hydrocarbons, such as ethane, propane, butane and pentane; for example, a propylene-propane mixture may constitute the feed. This makes it possible to use ordinary refinery streams without special preparation. Likewise, diluents such as nitrogen and the oxides of carbon may be present in the reaction mixture without deleterious effect.

In its preferred aspect, the process comprises contacting a mixture comprising propylene or isobutylene, ammonia and oxygen with the catalyst at an elevated temperature and at atmospheric or near atmospheric pressure.

Any source of oxygen may be employed in this process. For economic reasons, however, it is preferred that air be employed as the source of oxygen. From a purely technical viewpoint, relatively pure molecular oxygen will give equivalent results. The molar ratio of oxygen to the olefin in the feed to the reaction vessel should be in the range of 0.5:1 to 4:1 and a ratio of about 1:1 to 3:1 is preferred.

The molar ratio of ammonia to olefin in the feed to the reaction may vary between about 0.5:1 to 5:1. There is no real upper limit for the ammonia-olefin ratio, but there is generally no reason to exceed the 5:1 ratio. At ammonia-olefin ratios appreciably less than the stoichiometric ratio of 1:1, various amounts of oxygenated derivatives of the olefin will be formed. Outside the upper limit of this range only insignificant amounts of aldehydes and acids will be produced, and only very small amounts of nitriles will be produced at ammonia-olefin ratios below the lower limit of this range. It is unexpected that within the ammonia-olefin range stated, maximum utilization of ammonia is obtained, and this is highly desirable. It is generally possible to recycle any unreacted olefin and unconverted ammonia.

We have found that in many cases water in the mixture fed to the reaction vessel improves the selectivity of the reaction and yield of nitrile. However, reactions not including water in the feed are not to be excluded from this invention, inasmuch as water is formed in the course of the reaction.

In general, the molar ratio of added water to olefin, when water is added, is at least about 0.25:1. Ratios on the order of 1:1 to 4:1 are particularly desirable, but higher ratios may be employed, i.e., up to about 10:1.

The reaction is carried out at a temperature within the range of from about 500° to about 1100° F. The preferred temperature range is from about 600° to 900° F.

The pressure at which reaction is conducted is also an important variable, and the reaction should be carried out at about atmospheric or slightly above atmospheric (2 to 3 atmospheres) pressure. In general, high pressures, i.e., about 250 p.s.i.g., are not suitable since higher pressures tend to favor the formation of undesirable by-products.

The apparent contact time is not critical, and contact times in the range of from 0.1 to about 50 seconds may be employed. The optimum contact time will, of course, vary depending upon the olefin being treated, but in general, a contact time of from 1 to 15 seconds is preferred.

In general, any apparatus of the type suitable for carrying out oxidation reactions in the vapor phase may be employed in the execution of this process. The process may be conducted either continuously or intermittently. The catalyst bed may be a fixed-bed employing a large particulate or pelleted catalyst or, in the alternative, a so-called "fluidized" bed of catalyst may be employed. The fluid reactor may comprise an open column or the reactor may contain a plurality of perforated trays stacked horizontally throughout the length of the column, as described in U.S. Pat. No. 3,230,246 issued Jan. 18, 1966.

The reactor may be brought to the reaction temperature before or after the introduction of the reaction feed mixture. However, in a large scale operation, it is preferred to carry out the process in a continuous manner, and in such a system the circulation of the unreacted olefin is contemplated. Periodic regeneration or reactivation of the catalyst is also contemplated, and this may be accomplished, for example, by contacting the catalyst with air at an elevated temperature.

The products of the reaction may be recovered by any of the methods known to those skilled in the art. One such method involves scrubbing the effluent gases from the reactor with cold water or an appropriate solvent to remove the products of the reaction. If desired, acidified water can be used to absorb the products of reaction and neutralize unconverted ammonia. The ultimate recovery of the products may be accomplished by conventional means. The efficiency of the scrubbing operation may be improved when water is employed as the scrubbing agent by adding a suitable wetting agent in the water. Where molecular oxygen is employed as the oxidizing agent in this process, the resulting product mixture remaining after the removal of the nitriles may be treated to remove carbon dioxide with the remainder of the mixture containing the unreacted olefin and oxygen being recycled through the reactor. In the case where air is employed as the oxidizing agent in lieu of molecular oxygen, the residual product after separation of the nitriles and other carbonyl products may be scrubbed with non-polar solvent, e.g., a hydrocarbon fraction in order to recover unreacted olefin, and in this case the remaining gases may be discarded. The addition of a suitable inhibitor to prevent polymerization of the unsaturated products during the recovery steps is also contemplated.

SPECIFIC EMBODIMENTS

Comparative Examples A and B and Examples 1–3—Ammoxidation of propylene

Catalysts of the invention containing tantalum or samarium were prepared in the same manner as the two catalysts described below.

A catalyst having the composition 82.5 wt. % -$Ni_{10.5}FeBiPMo_{12}O_{57}$-17.5 wt. %-$SiO_2$ was prepared as follows:

229.3 grams of $(NH_4)(6Mo_7O_{27}\cdot 4H_2O)$ were dissolved in water with a minimum amount of heating. 12.5 grams of $H_3PO_4$ (85 wt. %) and 228 grams of DuPont Ludox AS (30 wt. %) colloidal silica sol were added in succession with stirring. 330.4 grams of $Ni(NO_3)_2\cdot 6H_2O$ dissolved in water were added to the slurry and stirred for 15 minutes. 43.8 grams of $Fe(NO_3)_3\cdot 9H_2O$ dissolved in water were added to this slurry followed by the addition of 52.5 grams of $Bi(NO_3)_3\cdot 5H_2O$ dissolved in water containing 5.3 cc. of concentrated $HNO_3$(60 wt. %). The slurry was stirred constantly for about 15 minutes.

The slurry was then spray dried and the powder obtained from the spray drier was further dried in an oven at 230° F. for 16 hours. The resulting dry powder was well mixed with 1 wt. % graphite and compacted into 1/16"×3/16" pellets with a convention pelleting machine. The pellets were heated for five hours at 446° F. to decompose the nitrates and were then calcined for twenty hours at 1022° F. The pelleted catalyst was crushed and sized to 20–35 Tyler mesh size.

In an alternate method a catalyst having the composition 80 wt. % $Ni_{4.5}Co_4FeBiAs_{0.5}P_{0.5}Mo_{12}O_{54}$-20 wt. %-$SiO_2$ was prepared by co-gelling the ingredients according to the following procedure:

A mixture of 76.4 grams $(NH_4)_6Mo_7O_{24}\cdot 4H_2O$,
2.1 grams $H_3PO_4$(85%),
2.7 grams $H_3As_3O_4\cdot \frac{1}{2}H_2O$,
85.0 grams $SiO_2$, (Ludox AS, 30% silica sol),
47.2 grams $Ni(NO_3)_2\cdot 6H_2O$ and
41.9 grams $Co(NO_3)_2\cdot 6H_2O$
was dissolved in water and stirred for 15 minutes. To this slurry was added an aqueous solution containing 14.6 grams of $Fe(NO_3)_3\cdot 9H_2O$ and 17.5 grams of $Bi(NO_3)_3\cdot 5H_2O$ previously dissolved in 20 cc. of a 10% $HNO_3$ solution. The combined mixtures were heated with constant stirring until gel formation occurred. The gel was then dried at approximately 266° F. The resulting catalyst was heat treated at 800° F. for four hours, and at 1022° F. for 16 hours, and then was sized to 20–35 Tyler screen mesh.

The reactor was a standard reactor with a fixed catalyst bed. The catalyst volume was about 5 cc. and the catalyst mesh size was 20 to 35 Tyler screen mesh. The gases were metered to the reactor with rotameters. The products of the reaction were recovered by scrubbing the effluent gases from the reactor with water and were then analyzed by means of a gas chromatograph.

The results are stated using the following definition:

$$\frac{\text{moles of nitrile product obtained}}{\text{moles of olefin fed}} \times 100$$

Comparative Examples A and B show catalysts of the art.

The reaction was run using a reaction temperature of 752° F., a contact time of 2.9 seconds and a feed of propylene/ammonia/air of 1/1.5/11. The reaction was run for 15 minutes and product was collected for analysis over 30 minutes.

Table I

| | Ammoxidation of Propylene | |
|---|---|---|
| Example | Catalyst Composition | % Per Pass Conversion to Acrylonitrile |
| Comp. A | 50% $Bi_9PMo_{12}O_{52}$ 50% $SiO_2$ | 39.9 |
| Comp. B | 50% $Fe_{4.5}Bi_{4.5}PMo_{12}O_{56.5}$ 50% $SiO_2$ | 41.9 |
| 1 | 80% $Ta_{0.2}Ni_{2.5}Co_{4.5}Fe_3BiMo_{12}O_{55.5}$ 20% $SiO_2$ | 65.4 |
| 2 | 80% $Sm_{0.1}Ni_{10}Co_{0.3}FeBiPMo_{12}O_{57}$ 20% $SiO_2$ | 68.3 |
| 3 | 80% $Sm_{0.1}Ni_{5.25}Co_{5.25}FeBiPMo_{12}O_{57}$ 20% $SiO_2$ | 64.9 |

Examples 4–10—Ammoxidation of propylene using different catalysts

In the same manner as shown above, various catalysts of the invention were prepared and used in the ammoxidation of propylene. The reactant ratios were propylene/ammonia/air/steam of 1/1.1/10/4, the contact time was six seconds, the temperature was 400° F. All catalysts contained 20 weight percent silica. The results are given in Table II. The following definitions are used:

$$\% \text{ conversion} = \frac{\text{moles of propylene reacted} \times 100}{\text{moles of propylene fed}}$$

$$\% \text{ selectivity} = \frac{\text{moles of acrylonitrile formed} \times 100}{\text{moles of propylene reacted}}$$

Table II

| | Ammoxidation of Propylene | | | |
|---|---|---|---|---|
| | | Results, % | | |
| Example | Catalyst | Per Pass Yield | Conversion | Selectivity |
| 4 | $Ce_{1.5}[K_{0.1}Ni_{2.5}Co_{4.5}Fe_{1.5}BiP_{0.5}Mo_{12}O_x]$ | 74.0 | 96.6 | 77 |
| 5 | $La_{1.5}[K_{0.1}Ni_{2.5}Co_{4.5}Fe_{1.5}BiP_{0.5}Mo_{12}O_x]$ | 64.9 | 90.5 | 70 |
| 6 | $Eu_{1.5}[K_{0.1}Ni_{2.5}Co_{4.5}Fe_{1.5}BiP_{0.5}Mo_{12}O_x]$ | 78.0 | 96.7 | 81 |

Table II-continued

| | | Ammoxidation of Propylene | | |
|---|---|---|---|---|
| | | | Results, % | |
| Example | Catalyst | Per Pass Yield | Conversion | Selectivity |
| 7 | $Di_{1.5}[K_{0.1}Ni_{2.5}Co_{4.5}Fe_{1.5}BiP_{0.5}Mo_{12}O_x]$ | 55.2 | 85.7 | 64 |
| 8 | $Ce_{0.5}[K_{0.1}Ni_{2.5}Co_{4.5}Fe_3Bi_{0.5}P_{0.5}Mo_{12}O_x]$ | 71.2 | 88.7 | 80 |
| 9 | $La_{0.5}[K_{0.1}Ni_{2.5}Co_{4.5}Fe_3Bi_{0.5}P_{0.5}Mo_{12}O_x]$ | 79.1 | 98.9 | 80 |
| 10 | $Sm_{0.5}[K_{0.1}Ni_{2.5}Co_{4.5}Fe_3Bi_{0.5}P_{0.5}Mo_{12}O_x]$ | 76.4 | 98.3 | 78 |

Examples 11–18—Ammoxidation at high olefin throughput

A catalyst of 80% $Nb_{0.5}K_{0.1}Ni_{2.5}Co_{4.5}Fe_3BiMo_{12}O_x$ and 20% silica was prepared by dissolving 31.8 g. of $(NH_4)_6Mo_7O_{24}.4H_2O$ in water, adding to this solution 2.0 g. of $NbCl_2$ slurried with water and 26.5 g. of 40% Nalco silica sol was added. A mixture of 10.9 g. of $Ni(NO_3)_2.6H_2O$ and 19.7 g. of $Co(NO_3)_2.6H_2O$ dissolved in water was added to the resulting slurry.

Separately, an aqueous solution of 18.2 g. $Fe(NO_3)_3.9H_2O$, 7.2 g. $Bi(NO_3)_3.5H_2O$ and 0.19 g. of a 45% aqueous solution of KOH was added. This solution was added to above slurry with stirring and heating. The mixture was evaporated to dryness, dried over night at 250° C., and heat treated at 550° F. for five hours, 800° F. for four hours, and 1020° F. for 16 hours.

In the same manner, other catalysts of the invention shown in Table III were prepared. These catalysts were used in the preparation of acrylonitrile using the reactor described above. The feed was propylene/ammonia/oxygen/nitrogen/steam of 1.8/2.2/3.6/2.4/6, the contact time was three seconds and the temperature was 420° F. Each of the catalysts have the basic structure $X_aK_{0.1}Ni_{2.5}Co_{4.5}Fe_3BiMo_{12}O_x$ and contain 20% by weight silica. The results of these experiments are shown in Table III.

Table III

| | | Ammoxidation of Propylene | | |
|---|---|---|---|---|
| | | | Results, % | |
| Example | Xa = | Per Pass Yield | Conversion | Selectivity |
| 11 | $Nb_{0.5}$ | 79.3 | 99.9 | 79 |
| 12 | $Nb_{1.0}$ | 79.9 | 97.2 | 82 |
| 13 | $Pr_{0.5}$ | 75.4 | 100.0 | 75 |
| 14 | $La_{0.5}$ | 74.0 | 100.0 | 74 |
| 15 | $Dy_{0.5}$ | 79.2 | 98.7 | 80 |
| 16 | $Ta_{0.5}$ | 78.8 | 97.4 | 81 |
| 17 | $Gd_{0.5}$ | 75.0 | 87.7 | 86 |
| 18 | $Yb_{0.5}$ | 75.0 | 99.7 | 75 |

In the same manner as shown by the examples above, isobutylene is reacted to give methacrylonitrile using catalysts of the invention.

Examples 19–28—Higher catalyst vent treatment

In the same manner as shown above, various catalysts of the invention were prepared and heat treated, except that an additional heat treatment for three hours at 650° C. was given. The reactions were run in a 5 cc. reactor, at 420° C. and a contact time of six seconds using a feed of propylene/ammonia/air/steam of 1/1.1/10/4. All catalysts contained 20% silica. The catalyst compositions and results are shown in Table IV.

Table IV

| | | Ammoxidation of Propylene | | |
|---|---|---|---|---|
| | | | Results, % | |
| Example | Catalyst | Per Pass Yield | Conversion | Selectivity |
| 19 | $Nd_{0.67}(K_{0.1}Ni_{2.5}Co_{3.5}Fe_3BiP_{0.5}Mo_{12}O_x)$ | 79.3 | 91.4 | 87 |
| 20 | $Di_{0.67}(K_{0.1}Ni_{2.5}Co_{3.5}Fe_3BiP_{0.5}Mo_{12}O_x)$ | 76.4 | 94.0 | 81 |
| 21 | $Yb_{0.67}(K_{0.1}Ni_{2.5}Co_{3.5}Fe_3BiP_{0.5}Mo_{12}O_x)$ | 74.9 | 90.2 | 83 |
| 22 | $Di_{1.5}K_{0.1}Ni_{2.5}Co_{4.5}Fe_{1.5}BiP_{0.5}Mo_{12}O_x$ | 75.3 | 95.5 | 79 |
| 23 | $Di_{0.5}(K_{0.1}Ni_{2.5}Co_{4.5}Fe_3Bi_{0.5}P_{0.5}Mo_{12}O_x)$ | 81.6 | 96.1 | 85 |
| 24 | $Ce_{0.5}(K_{0.1}Ni_{2.5}Co_{4.5}Fe_3Bi_{0.5}P_{0.5}Mo_{12}O_x)$ | 75.7 | 86.9 | 87 |
| 25 | $Nd_{0.5}(K_{0.1}Ni_3Co_5Fe_3Bi_{0.5}P_{0.5}Mo_{12}O_x)$ | 77.1 | 96.0 | 80 |
| 26 | $Yb_{0.5}(K_{0.1}Ni_3Co_5Fe_3Bi_{0.5}P_{0.5}Mo_{12}O_x)$ | 80.4 | 97.1 | 83 |
| 27 | $Nb_{0.5}K_{0.1}Ni_{2.5}Co_{4.5}Fe_3BiMo_{12}O_x$ | 82.9 | 95.6 | 87 |
| 28 | $Nd_{0.5}K_{0.1}Ni_{2.5}Co_{4.5}Fe_3BiP_{0.5}Mo_{12}O_x$ | 71.5 | 90.2 | 79 |

It will therefore be appreciated from the foregoing examples that samarium, cerium, lanthanum, europium, dysprosium, praseodymium, gadolinium, ytterbium, neodymium and didynium are especially useful as component A in the above noted formula, while the other rare earth, namely terbium, holmium, erbium, thulium and lutetium as well as promethium, if available, are also useful.

We claim:

1. A catalyst having the formula

$$A_aD_gE_bG_cFe_dBi_3Mo_{12}O_x$$

wherein
A is a rare earth metal or mixture thereof;
D is an alkali metal;
E is nickel, cobalt, magnesium, zinc, cadmium, calcium or mixture thereof;
G is phosphorus, boron, arsenic, or mixtue thereof;
and wherein
a is greater than zero to about 3;
b is about 0.1 to about 20;
c is 0 to about 3;
d is about 0.1 to about 8;
e is about 0.1 to about 6;
f is about 8 to about 16;
g is greater than zero to about 3; and
x is a number determined by the valence requirements of the other elements present.

2. The catalyst of claim 1 wherein E is nickel, cobalt, magnesium or mixtures thereof.

3. The catalyst of claim 1 wherein E is nickel, cobalt or mixtures thereof.

4. The catalyst of claim 1 wherein G is phosphorous, arsenic or mixtures thereof.

5. Catalyst having the formula $$Ta_a D_g E_b G_c Fe_d Bi_e Mo_{12} O_x$$

wherein
D is an alkali metal;
E is nickel, cobalt, magnesium, zinc, cadmium, calcium or mixture thereof;
G is phosphorus, boron, arsenic, or mixture thereof;
and wherein
a is greater than zero to about 3;
b is about 0.1 to about 20;
c is 0 to about 3;
d is about 0.1 to about 8;
e is about 0.1 to about 6;
f is about 8 to about 16;
g is greater than zero to about 3; and
x is a number determined by the valence requirements of the other elements present.

6. Catalyst having the formula $$Nb_a D_g E_b G_c Fe_d Bi_e Mo_{12} O_x$$

wherein
D is an alkali metal;
E is nickel, cobalt, magnesium, zinc, cadmium, calcium or mixture thereof;
G is phosphorus, boron, arsenic or mixture thereof;
and wherein
a is greater than zero to about 3;
b is about 0.1 to about 20;
c and g are 0 to about 3;
d is about 0.1 to about 8;
e is about 0.1 to about 6;
f is about 8 to about 16; and
x is a number determined by the valence requirements of the other elements present.

* * * * *